US012758688B2

(12) United States Patent
Herbst et al.

(10) Patent No.: US 12,758,688 B2
(45) Date of Patent: Oct. 13, 2026

(54) MEDICAL DEVICES INCLUDING THERAPEUTIC COATINGS FOR LOCAL DELIVERY OF A DIRECT ANTICOAGULANT

(71) Applicant: Boston Scientific Scimed, Inc., Maple Grove, MN (US)

(72) Inventors: Thomas John Herbst, Coon Rapids, MN (US); Edward Kopesky, Mahtomedi, MN (US); Steven L. Kangas, Woodbury, MN (US); Hongxia Zeng, Maple Grove, MN (US); Aaron Cooper Foss, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 350 days.

(21) Appl. No.: 18/632,758

(22) Filed: Apr. 11, 2024

(65) Prior Publication Data

US 2024/0342348 A1 Oct. 17, 2024

Related U.S. Application Data

(60) Provisional application No. 63/579,191, filed on Aug. 28, 2023, provisional application No. 63/458,731, filed on Apr. 12, 2023.

(51) Int. Cl.
*A61L 31/10* (2006.01)
*A61L 29/08* (2006.01)
(Continued)

(52) U.S. Cl.
CPC ......... *A61L 33/0041* (2013.01); *A61L 29/085* (2013.01); *A61L 29/16* (2013.01);
(Continued)

(58) Field of Classification Search
CPC .... A61L 29/085; A61L 26/0014; A61L 31/10; A61F 2/82; A61F 2/844
See application file for complete search history.

(56) References Cited

U.S. PATENT DOCUMENTS 7,157,456 B2 1/2007 Straub et al.
7,741,273 B2 * 6/2010 McKay .................. A61P 29/00 514/630

(Continued)

FOREIGN PATENT DOCUMENTS

CA 3220615 A1 1/2023
WO 2021242783 A1 12/2021

OTHER PUBLICATIONS

Arai et al., Development of a Stent Capable of the Controlled Release of Basic Fibroblast Growth Factor and Argatroban to Treat Cerebral Aneurysms: In Vitro Experiment and Evaluation in a Rabbit Aneurysm Model, Journal of Biomedical Materials Research Part B: Applied Biomaterials, vol. 107, No. 6, 10 pages. Jan. 17, 2019.

(Continued)

*Primary Examiner* — Kevin T Truong
(74) *Attorney, Agent, or Firm* — SEAGER, TUFTE & WICKHEM, LLP

(57) ABSTRACT

A medical device may be coated with a therapeutic composition that includes a direct oral anticoagulant. An illustrative drug coating composition may comprise an excipient including polylactic acid (PLA), poly(lactic-co-glycolic acid) (PLGA), or poly(vinylidene fluoride)-co-hexafluoropropylene (PVDF-HFP) and a direct oral anticoagulant (DOAC). The illustrative drug coating may be applied to an outer surface of a medical device.

6 Claims, 7 Drawing Sheets

(51) Int. Cl.
*A61L 29/16* (2006.01)
*A61L 31/16* (2006.01)
*A61L 33/00* (2006.01)

(52) U.S. Cl.
CPC ............... *A61L 31/10* (2013.01); *A61L 31/16* (2013.01); *A61L 2300/204* (2013.01); *A61L 2300/216* (2013.01); *A61L 2300/416* (2013.01); *A61L 2300/42* (2013.01); *A61L 2300/61* (2013.01); *A61L 2300/622* (2013.01); *A61L 2300/802* (2013.01); *A61L 2420/02* (2013.01); *A61L 2420/08* (2013.01)

(56) References Cited

U.S. PATENT DOCUMENTS 8,377,461 B2 2/2013 Chinn et al.
8,409,272 B2 4/2013 Omura et al.
8,430,861 B2 4/2013 Schwartz et al.
8,585,642 B2 11/2013 Doshi et al.
8,628,790 B2 1/2014 To et al.
8,778,013 B2 7/2014 Doshi et al.
8,784,860 B2 7/2014 Falotico et al.
9,034,363 B2 5/2015 Doshi et al.
9,943,315 B2 4/2018 Kaplan et al.
9,981,058 B2 5/2018 Orlowski
10,154,856 B2 12/2018 Sillender
10,722,240 B1 7/2020 Melanson et al.
10,918,510 B2 2/2021 Cully et al.
11,026,695 B2 6/2021 Melanson et al.
11,318,331 B2 5/2022 Shabtay et al.
11,654,036 B2 5/2023 Sirhan et al.
11,931,560 B2 3/2024 Nitzan et al.
12,029,755 B2 7/2024 Kanthi et al.
2003/0158120 A1 8/2003 Mattsson
2005/0064006 A1 3/2005 Perzborn et al.
2008/0097575 A1* 4/2008 Cottone .................. A61F 2/844
623/1.42
2008/0241215 A1 10/2008 Falotico et al.
2008/0243241 A1 10/2008 Zhao
2010/0003542 A1 1/2010 Perzborn et al.
2010/0130543 A1 5/2010 Gant et al.
2016/0213499 A1 7/2016 Zheng et al.
2016/0331564 A1 11/2016 Kangas
2016/0367785 A1 12/2016 Schwartz et al.
2018/0000750 A1 1/2018 Tseng et al.
2021/0339003 A1 11/2021 Das et al.
2023/0011767 A1 1/2023 Kangas et al.
2023/0052812 A1 2/2023 Kangas et al.
2023/0134031 A1 5/2023 Stacey et al.
2023/0165874 A1 6/2023 Yan et al.
2024/0226517 A9 7/2024 Li et al.
2024/0342348 A1 10/2024 Herbst et al.
2024/0424175 A1 12/2024 Yan et al.
2026/0060821 A1* 3/2026 Kangas ..................... A61F 2/82

OTHER PUBLICATIONS

International Search Report and Written Opinion for International Application No. PCT/US2024/024701, dated Jul. 5, 2024. (15 pages).

* cited by examiner

MEDICAL DEVICES INCLUDING THERAPEUTIC COATINGS FOR LOCAL DELIVERY OF A DIRECT ANTICOAGULANT

CROSS-REFERENCE TO RELATED APPLICATIONS

This application claims the benefit of priority under 35 U.S.C. § 119 of U.S. Provisional Patent Application Ser. No. 63/579,191 filed on Aug. 28, 2023 and U.S. Provisional Patent Application Ser. No. 63/458,731 filed on Apr. 12, 2023, the entire disclosure of which is hereby incorporated by reference.

TECHNICAL FIELD

The present disclosure pertains to medical devices and more particularly to medical devices that include a therapeutic coating that locally delivers a direct acting anticoagulant.

BACKGROUND

A wide variety of medical devices have been developed for medical use, for example, intravascular and/or intracardiac use. Some of these devices include guidewires, catheters, balloons, stents, and the like. These devices are manufactured by any one of a variety of different manufacturing methods and may be used according to any one of a variety of methods. Some of these medical devices may include a therapeutic agent. Of the known medical devices and methods, each has certain advantages and disadvantages. There is an ongoing need to provide alternative medical devices as well as alternative methods for manufacturing and using medical devices. This may include the formation of therapeutic agents that locally delivery a direct anticoagulant.

SUMMARY

The present disclosure pertains to medical devices and more particularly to medical devices that include a therapeutic coating that is locally active and bioresorbable in a reversible thermo-gelling excipient.

In a first example, a drug coating composition may comprise an excipient comprising polylactic acid (PLA), poly(lactic-co-glycolic acid) (PLGA), or poly(vinylidene fluoride)-co-hexafluoropropylene (PVDF-HFP) and a direct oral anticoagulant (DOAC).

Alternatively or additionally to any of the examples above, in another example, the DOAC may be apixaban, rivaroxaban, or edoxaban.

Alternatively or additionally to any of the examples above, in another example, the DOAC may be present in the drug coating composition in a range of about 5 weight percent to about 40 weight percent.

Alternatively or additionally to any of the examples above, in another example, the DOAC may be present in the drug coating composition in an amount of between 100-4000 nanograms per square millimeter.

Alternatively or additionally to any of the examples above, in another example, the drug coating composition may further comprise an antiproliferative.

Alternatively or additionally to any of the examples above, in another example, the antiproliferative may comprise one or more of paclitaxel, everolimus, sirolimus, and rapamycin.

Alternatively or additionally to any of the examples above, in another example, the drug coating composition may further comprise an antioxidant.

In another example, a balloon catheter may comprise an elongated shaft, an inflatable balloon coupled to a distal portion of the elongated shaft, and a drug coating composition disposed on an outer surface of the inflatable balloon. The drug coating composition may comprise an excipient and a direct oral anticoagulant (DOAC).

Alternatively or additionally to any of the examples above, in another example, the excipient may comprise polylactic acid (PLA) or poly(lactic-co-glycolic acid) (PLGA).

Alternatively or additionally to any of the examples above, in another example, the DOAC may be rivaroxaban.

Alternatively or additionally to any of the examples above, in another example, the excipient may comprise in the range of about 60 to 95 weight percent of the drug coating composition and the DOAC may comprise in the range of about 5 to 40 weight percent of the drug coating composition.

Alternatively or additionally to any of the examples above, in another example, the drug coating composition may further comprise an antiproliferative.

Alternatively or additionally to any of the examples above, in another example, the antiproliferative may comprise one or more of paclitaxel, everolimus, sirolimus, and rapamycin.

Alternatively or additionally to any of the examples above, in another example, the antiproliferative may be provided as a second layer.

Alternatively or additionally to any of the examples above, in another example, the excipient may further comprise ethyl cellulose or acetyl tri-butyl citrate (ATBC).

In another example, a stent may comprise an elongated tubular body having a strut framework and a drug coating composition disposed on an outer surface of the strut framework. The drug coating composition may comprise an excipient and a direct oral anticoagulant (DOAC).

Alternatively or additionally to any of the examples above, in another example, the excipient may comprise poly(vinylidene fluoride)-co-hexafluoropropylene (PVDF-HFP).

Alternatively or additionally to any of the examples above, in another example, the DOAC may be rivaroxaban.

Alternatively or additionally to any of the examples above, in another example, the excipient may comprise in the range of about 55 to 95 weight percent of the drug coating composition and the DOAC may comprise in the range of about 5 to about 45 weight percent of the drug coating composition.

Alternatively or additionally to any of the examples above, in another example, the drug coating composition may further comprise an antiproliferative.

Alternatively or additionally to any of the examples above, in another example, the stent may further comprise a topcoat disposed over the drug coating composition, the topcoat free from a therapeutic agent.

Alternatively or additionally to any of the examples above, in another example, the topcoat may comprise PVDF-HFP.

In another example, a method for manufacturing a drug coating composition may comprise dissolving polylactic acid (PLA) or poly(lactic-co-glycolic acid) (PLGA) and rivaroxaban in a mixture of dichloromethane and dimethylformamide to form a first solution, adding the first solution to aqueous poly(vinyl acid) PVA while mixing to form a bead solution, filtering the bead solution to collect a plurality of microspheres, and drying the plurality of microspheres.

Alternatively or additionally to any of the examples above, in another example, the PLA or PLGA and rivaroxaban may be dissolved at a ratio of in the range of about 85 to 95 weight percent PLA or PLGA to about 5 to about 15 weight percent rivaroxaban.

Alternatively or additionally to any of the examples above, in another example, the mixture of dichloromethane and dimethylformamide may be about 75 weight percent dichloromethane and about 25 weight percent dimethylformamide.

Alternatively or additionally to any of the examples above, in another example, the aqueous PVA may be about 2% PVA.

Alternatively or additionally to any of the examples above, in another example, the method may further comprise adding the bead solution to a 0.1% solution of aqueous PVA and mixing for a first period of time.

Alternatively or additionally to any of the examples above, in another example, the first period of time may be in the range of about 1 to about 3 hours.

Alternatively or additionally to any of the examples above, in another example, drying the plurality of microspheres may include drying the microspheres under vacuum at room temperature for a second period of time.

Alternatively or additionally to any of the examples above, in another example, the second period of time may be in the range of about 2 days to about 4 days.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
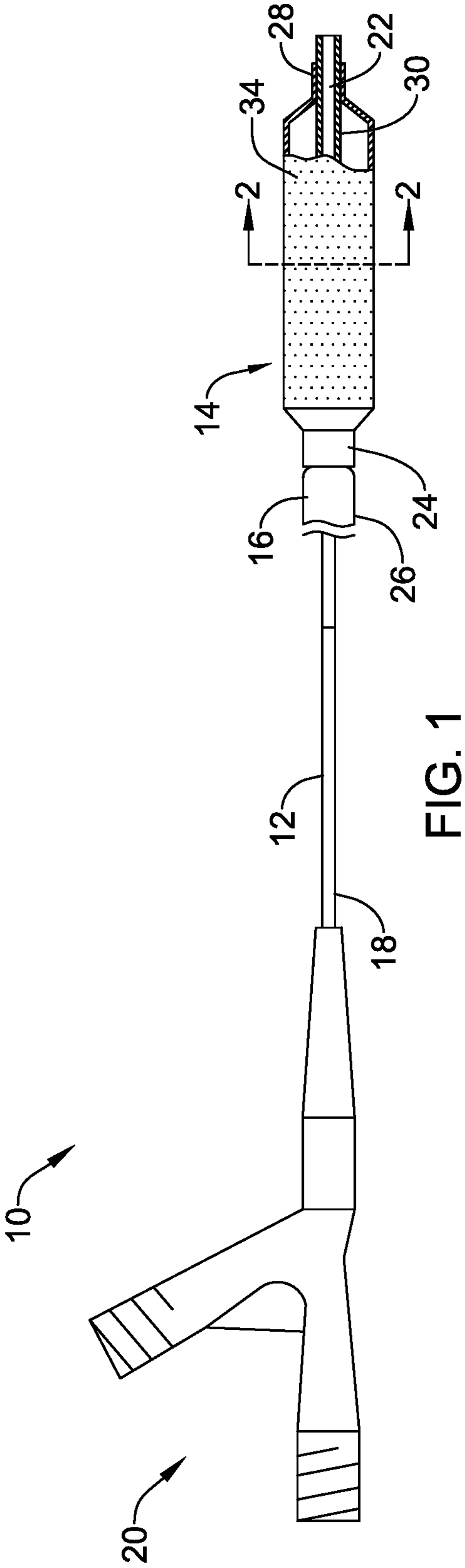
FIG. 1 is a schematic side view of an example drug delivery balloon catheter.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Deep vein thrombosis (DVT) of the lower limbs may affect up to 900,000 people in the United States per year. DVT can be broken down into three different phases: the acute phase, the sub-acute phase (onset of post thrombotic syndrome (PTS)), and the chronic phase (PTS). Within the acute phase, damaged endothelial cells may express tissue factor, release von Willebrand factor and P-selectin, and yield E-selectin, all prompting and amplifying coagulation. The heightened coagulation may result in an increased inflammatory response. The sub-acute phase sees a maximum inflow of monocytes leading to thrombus resolution and creating inflammatory reactions guided by reduced flow and reduced oxygenation. When thrombus resolution is inhibited, circulating progenitor cells can cause damage to the vein wall. The chronic phase is described as point in which the thrombus contains primarily collagen and high monocytes counts. At this point, venous outflow is obstructed or restricted due to flawed fibrinolysis and incomplete improper revascularization.

In the range of about 25-50% of patients with proximal DVTs go on to develop PTS. PTS may be caused by fibrotic tissue blocking the normal path of blood flow through one's vessels. With this blockage, blood accumulates in the veins, resulting in improper function of the veins and unhealthy pressure levels within the vein walls. Symptoms and complications of PTS include, but are not limited to, swelling of the leg (edema), throbbing pain in the leg, skin dryness, discolorations of the skin, heaviness and tiredness of the leg, ulcers, repeat thrombosis, and a general reduction in the quality of life. In some cases, PTS can be debilitating. PTS may develop as a consequence of venous hypertension which may be a result of both valvular dysfunction which leads to valvular reflux and persistent partial venous occlusion.

Blood coagulation factor Xa (FXa) is a serine protease that is involved in both the blood coagulation cascade and in the expression of numerous inflammatory cytokines such as IL-6. FXa is known to activate prothrombin to thrombin which eventually leads to the formation of cross-linked blood clots. Further, FXa has also been linked to inflammation via protease-activated receptors. Drugs (such as, but not limited to, direct oral anti-coagulants (DOACs) such as rivaroxaban and apixaban) that directly bind and inhibit factor Xa are highly effective at preventing thrombus formation in patients with atrial fibrillation (A-fib) and in DVT patients at reducing the risk of recurrent DVT. In addition, clinical studies have shown that oral rivaroxaban significantly reduces the risk of PTS. This may be due in part to the anti-inflammatory properties of rivaroxaban. Clinical data suggests that anticoagulation may reduce the risk of PTS by up to 78%. The risk of PTS in DOAC-treated patients may be reduced by up to 54% compared to patients treated with conventional anticoagulation (e.g., warfarin).

Mechanistically, in human aortic endothelial cells, FXa stimulation increased the expression of inflammatory cytokines (interleukin (IL)-1β, IL-6, IL-8, monocyte chemoattractant protein-1) and adhesive molecules (which may all be reversed by the cotreatment of a DOAC such as rivaroxaban). Further, FXa may promote both the proliferation and the migration of vascular smooth muscle cells, which may be blocked in the presence of a DOAC. Increased levels of inflammatory cytokines such as interleukin-6 (IL-6) have been linked to the development of PTS. Inflammation may play a role in promoting PTS by delaying thrombus resolution and by inducing vein wall fibrosis, which promotes valvular reflux. Studies using a mouse DVT model have shown that mice treated with anti-IL-6 showed less thrombus weight, 44% lower intimal wall thickness, and 30% lower vein wall collagen formation compared to controls.

PTS patients with persistent venous occlusion may be often treated with bare metal stents. Vessel patency after stent placement may be fairly good but in-stent restenosis is a common problem. Analysis of in-stent restenosis of PTS patients shows that stenosis likely occurs through a process of thrombus formation, with the thrombus ultimately converting to and progressing via intimal hyperplasia. It may be desirable to provide a stent with a therapeutic coating that can reduce the risk of PTS.

It is further contemplated that it may be desirable to a provide an expandable balloon with a therapeutic coating that may reduce thrombus development and/or growth. For example, it may be desirable to deliver a drug or therapeutic agent to a passageway of the body, such as, but not limited to, native blood vessels, stented blood vessels, and body lumens. These passageways sometimes become occluded (for example, by a tumor, thrombus, atherosclerotic plaque, etc.). To widen an occluded body vessel, balloon catheters can be used, for example, in angioplasty. In some embodiments, a balloon catheter can include an inflatable and deflatable balloon carried by a long and narrow catheter body. The balloon can be initially folded around the catheter body to reduce the radial profile of the balloon catheter for easy insertion into the body. During use, the folded balloon can be delivered to a target location in the vessel, for example, a portion occluded by plaque, by threading the balloon catheter over a guide wire previously located in the vessel. The balloon is then inflated, for example, by introducing a fluid (such as a gas or a liquid) into the interior of the balloon. Inflating the balloon can radially expand the vessel so that the vessel can permit an increased rate of blood flow. After use, the balloon is typically deflated and withdrawn from the body. In some instances, it may be desirable to coat, layer, or otherwise apply a drug or therapeutic agent to an outer surface of the balloon to deliver and/or administer the drug or therapeutic agent to a lumen wall when the balloon is expanded. During deployment (e.g., expansion of the balloon), the coating including the drug or therapeutic agent may break apart into particulates. Some of the particulates may be partially deposited on the inner surface of the vessel.

While the therapeutic coating described herein is discussed relative to balloons, balloon catheters, and stents, it is contemplated that the therapeutic coating can be applied to and/or used in conjunction with other medical devices, such as, but not limited to, embolic filters, implantable devices, treatment devices, etc.

The medical devices disclosed herein may provide direct oral anticoagulants (DOACs) on the surface of a device. The device may then be delivered to where the local treatment is needed. This may provide the advantage of reducing the potential adverse effects of systemic oral anticoagulant (OAC) therapy. This may be accomplished by incorporating DOACs into a polymer coating disposed on one or more portions of medical device, such as, but not limited to a balloon or stent.

Unlike conventional anticoagulants such as heparin and warfarin which inhibit various cofactors in the internal and external clotting cascade, and which may contribute to the serious systemic negative effects, the category of anticoagulants known as direct oral anticoagulants (DOACs) bind directly to specific clotting factors. Examples of DOACs include apixaban, rivaroxaban, edoxaban, dabigatran, betrixaban, and argatroban, which directly bind to factor Xa, and dabigatran, which directly binds to factor IIa (thrombin). The medical devices disclosed herein provide a way of achieving localized release of these DOACs at the surface of the device.

Figure 2:
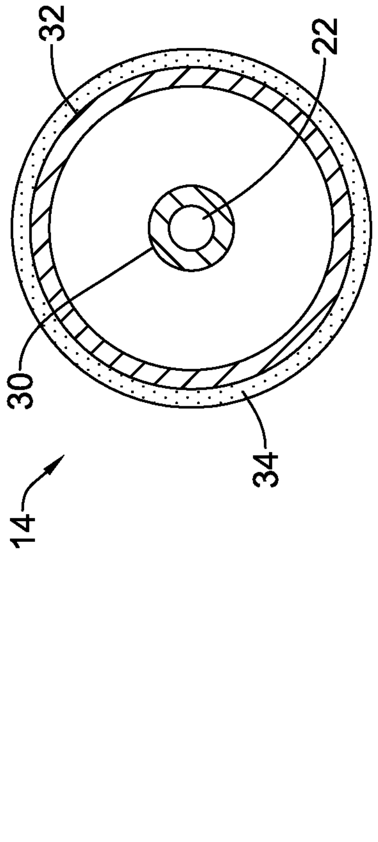
FIG. 2 is a cross-sectional view of a catheter-based balloon taken through line 2-2 in FIG. 1.

FIG. 1 is a schematic side view of a drug delivery balloon catheter 10. A cross-sectional view of the drug delivery balloon catheter 10 is shown in FIG. 2. In the illustrated embodiment, the catheter 10 may include an elongated shaft 12, an inflatable balloon 14 coupled at or to a distal portion 16 of the shaft 12, along with other components. The elongated shaft 12 may include a tubular member having a proximal portion 18, and one or more lumens extending between the proximal portion 18 and the distal portion 16. The elongated shaft 12 may be configured to have a substantially circular cross-section; however, it may be configured to have other suitable cross-sectional shapes, such as elliptical, oval, polygonal, irregular, etc. In addition, the elongated shaft 12 may be flexible along its entire length or adapted for flexure only along portions of its length. The required degree of flexibility of the elongated shaft 12 may be predetermined based on its intended navigation to a target vascular passage, and the amount of inertial force required for advancing the elongated shaft 12 through the vascular passage. The catheter 10 may be configured as an over-the-wire (OTW) catheter, a single-operator exchange (SOE) catheter, a fixed wire catheter, and/or the like.

The cross-sectional dimensions of the elongated shaft 12 may vary according to the desired application. Generally, the cross-sectional dimensions of the elongated shaft 12 may be sized smaller than the typical blood vessel in which the catheter 10 is to be used. The length of the elongated shaft 12 may vary according to the location of the vascular passage where drug delivery is desired. In some instances, a 6F or a 5F catheter may be used as the elongated shaft 12, where "F," also known as French catheter scale, is a unit to measure catheter diameter (1F=⅓ millimeter (mm)). In addition, the elongated shaft 12 or a portion thereof may be selectively steerable. Mechanisms such as, pull wires and/or other actuators may be used to selectively steer the elongated shaft 12, if desired.

The proximal portion 18 of the elongated shaft 12 may include a handle 20 usable to manually maneuver the distal portion 16 of the elongated shaft 12. The handle 20 may include one or more ports that may be used to introduce any suitable medical device, fluid or other interventions. For example, the handle 20 may include a guidewire port in communication with a guidewire lumen 22 (shown in the cut-away portion at the distal end of the catheter 10 and also in FIG. 2) which may be used to introduce a guidewire having an appropriate thickness into the elongated shaft 12, which may guide the elongated shaft 12 to the target location within an artery. Furthermore, the handle 20 may include an inflation port configured to be coupled to a source of inflation fluid for delivering an inflation fluid through an inflation lumen of the catheter shaft 12 to the inflatable balloon 14. In certain embodiments, the elongated shaft 12 may include one or more additional lumens, which may be configured for a variety of purposes, such as delivering medical devices or for providing fluids, such as saline, to a target location.

The inflatable balloon 14 may be operably coupled at or to the distal portion 16 of the elongated shaft 12. In particular, a proximal portion or waist 24 of the inflatable balloon 14 may be secured to the distal portion 16 of the elongated shaft 12, such as an outer tubular member 26 of the elongated shaft 12. Furthermore, a distal portion or waist 28 of the inflatable balloon 14 may be secured to the distal portion 16 of the elongated shaft 12, such as an inner tubular member 30 of the elongate shaft 12 extending through the outer tubular member 26. A suitable securing method(s) may be employed to couple the two structures, including but not limited to adhesive bonding, thermal bonding (e.g., hot jaws, laser welding, etc.) or other bonding technique, as desired. The inflatable balloon 14 may be configured to be expanded from a deflated state to an inflated state through delivery of an inflation fluid (e.g., saline) through the inflation lumen of the catheter shaft 12. The balloon 14 may be deflated during introduction of the catheter inside the patient's body, whereas the balloon 14 may be inflated once it reaches the target site within the body vessel.

The inflatable balloon may be manufactured using or otherwise formed of any suitable material, including polymer materials, such as polyamide, polyether block amide (PEBA), polyester, nylon, etc. The inflatable balloon 14 may have a substantially cylindrical configuration with a circular cross-section, as shown in the illustrative embodiment. However, in other embodiments the inflatable balloon 14 may have another suitable configuration or shape, if desired.

The inflatable balloon 14 may include a balloon wall 32 have a drug coating 34 disposed thereon. In some cases, the drug coating or coating composition 34 may include a DOAC, such as, but not limited to rivaroxaban, as will be described in more detail herein. The drug coating 34 may be disposed along substantially the entire length and/or circumference of the balloon 14 or along one or more portions of the balloon 14. For example, the drug coating 34 may be disposed along a central or body portion of the balloon 14. The drug coating 34 disposed on the balloon 14/balloon wall 32 may have an average thickness in the range of about 1 micrometer (μm) to about 50 μm, for example.

Figure 3:
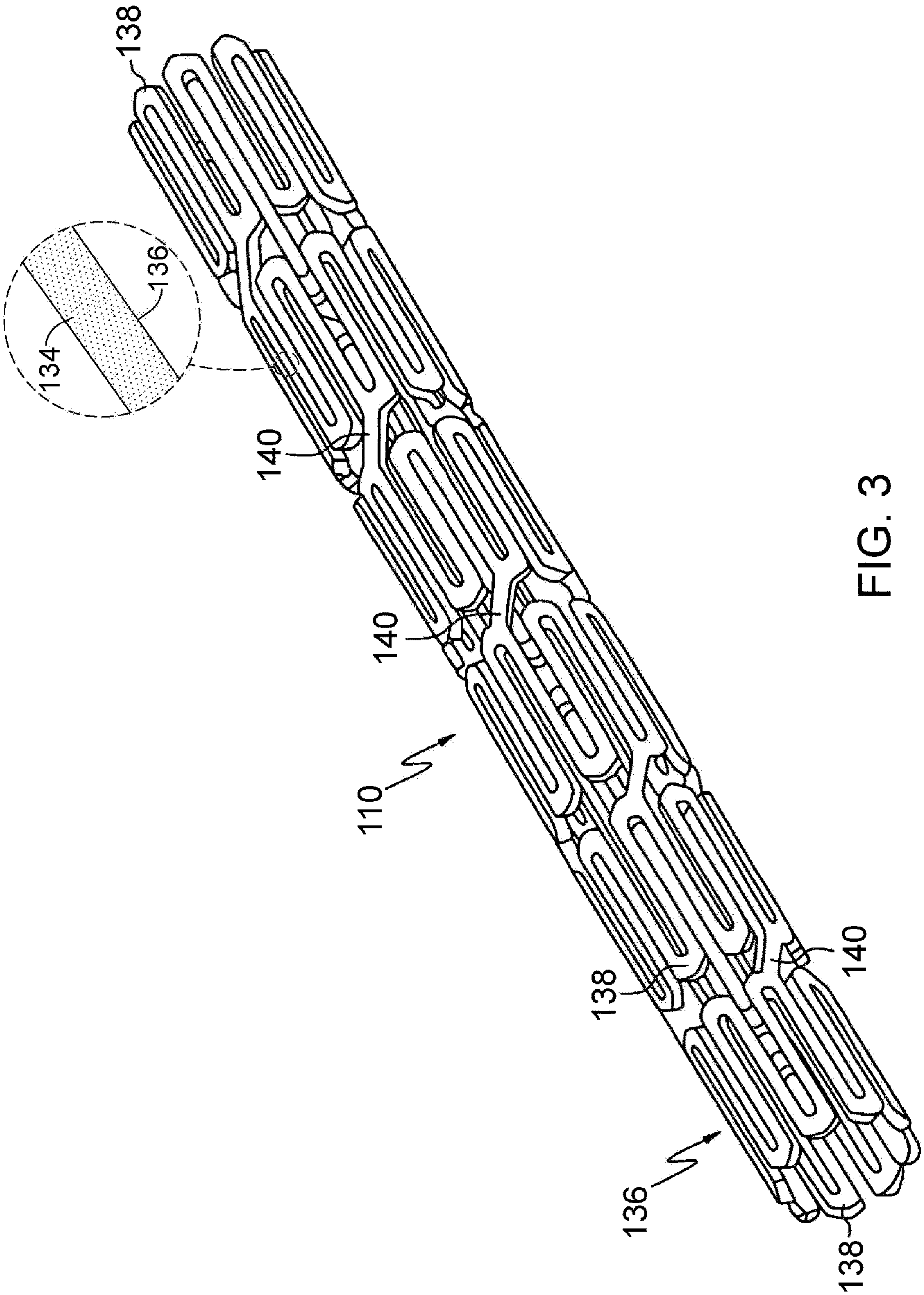
FIG. 3 depicts an example drug-coated stent in a collapsed or delivery configuration.
Figure 4:
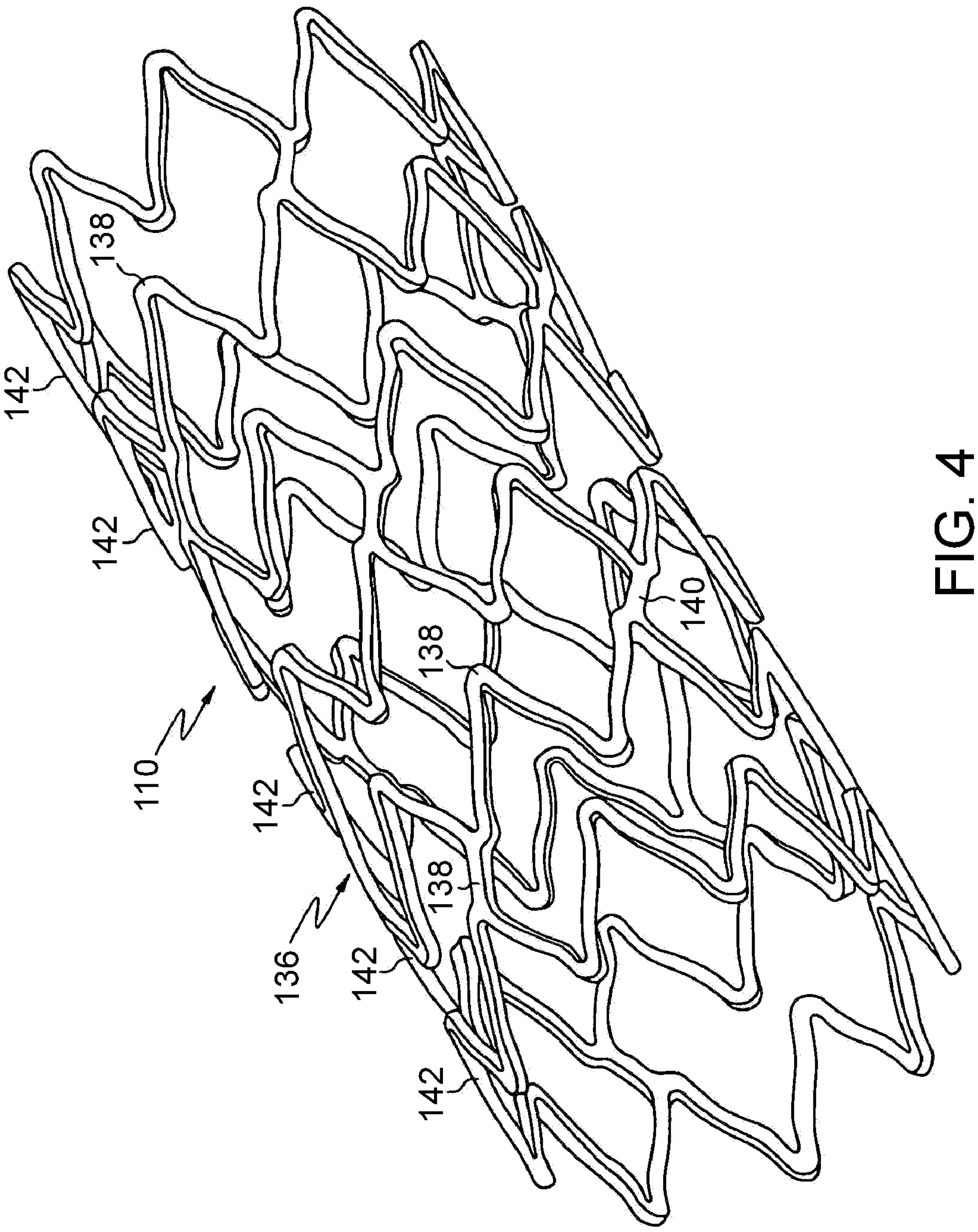
FIG. 4 depicts an example drug-coated stent in an expanded or deployed configuration.

FIGS. 3-4 illustrate an example drug-coated stent 110 in either a collapsed or delivery configuration (FIG. 3) or in an expanded or deployed configuration (FIG. 4). In general, the stent 110 may be delivered to a suitable target region via a catheter/delivery system while in the collapsed configuration. Upon reaching the target region, the stent 110 may expand or be expanded into the expanded configuration. The stent 110 may be self-expanding (e.g., the stent 110 may be formed from a shape memory material such as nitinol) or may be balloon expandable. When the stent 110 is self-expanding, the stent 110 may be held/constrained in the collapsed configuration during delivery and then unconstrained to allow the stent 110 to expand (e.g., self-expand) to the expanded configuration. When the stent 110 is balloon-expandable, the stent 110 may be constrained crimped onto a delivery device/catheter and then expanded (e.g., via an expandable member or balloon) when at/adjacent the target region.

The stent 110 may include an elongated tubular body having a strut framework 136. The strut framework 136 may define one or more peaks or apex regions 138 and/or one or more connecting regions 140. Intermediate regions 142 may interconnect the apex regions 138 and/or the connecting regions 140. In some instances, the stent 110 may be formed from a cut (e.g., laser cut) tube. In such instances, the structural arrangement of the apex regions, connecting regions 140, and/or intermediate regions 142 may be determined by the cut pattern. It can be appreciated that a wide variety of patterns/arrangement may be used for the stent 110. In other instances, the stent 110 may be a woven or braided stent, a stent formed from a flat sheet of material that is rolled into a stent formation, molded, cast, and/or the like.

Figure 6:
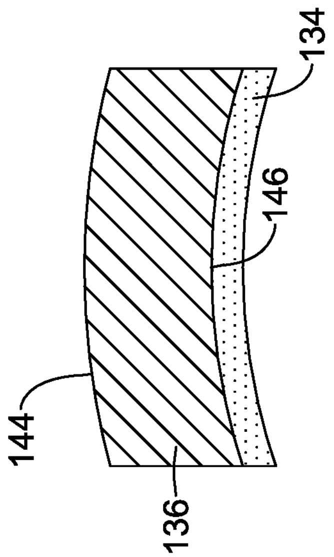
FIG. 6 schematically depicts a drug coating disposed along an inner or luminal surface of an example drug-coated stent.
Figure 7:
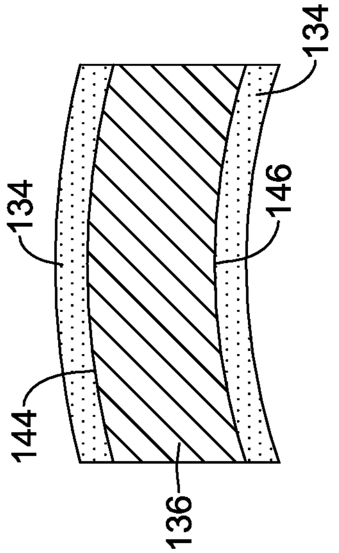
FIG. 7 schematically depicts the drug coating disposed along both an outer or abluminal surface of an example drug-coated stent and along an inner or luminal surface of the example drug-coated stent.
Figure 5:
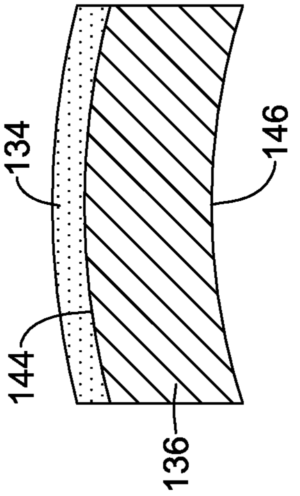
FIG. 5 schematically depicts a drug coating disposed along an outer or abluminal surface of an example drug-coated stent.

A drug coating or coating composition 134 may be disposed along the strut framework 136. For example, FIG. 5 schematically depicts the drug coating 134 disposed along an outer or abluminal surface 144 of the stent 110 (e.g., along the outer or abluminal surface 144 of the strut framework 136). FIG. 6 schematically depicts the drug coating 134 disposed along an inner or luminal surface 146 of the stent 110 (e.g., along the inner or luminal surface 146 of the strut framework 136). FIG. 7 schematically depicts the drug coating 134 along both an outer or abluminal surface 144 of the stent 110 and the inner or luminal surface 146 of the stent 110 (e.g., along both the outer or abluminal surface 144 of the strut framework 136 and the inner or luminal surface 146 of the strut framework 136). While not explicitly shown, in some examples, the drug coating 134 may be additionally or alternatively disposed along the lateral sides of the strut framework 136, the lateral sides extending between the outer or abluminal surface 144 and the inner or luminal surface 146. It is noted that FIGS. 5-7 are intended to represent, schematically, a cross-sectional view of a portion (e.g., a singular region or portion of a strut) of the strut framework 136. In these views, the strut framework 136 is depicted as being partially arcuate in shape. This is intended to correspond to the generally cylindrical shape of the stent 110, for example when the stent 110 is in the expanded configuration. In some cases, the drug coating 134 may include a DOAC, such as, but not limited to rivaroxaban, as will be described in more detail herein. The drug coating 134 disposed on the strut framework 136 may have an average thickness in the range of about 1 μm to about 50 μm, for example.

The terms "therapeutic agents," "drugs," "bioactive agents," "pharmaceuticals," "pharmaceutically active agents", and other related terms may be used interchangeably herein and include genetic therapeutic agents, non-genetic therapeutic agents, and cells. Therapeutic agents may be used singly or in combination. A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

The drug coating 34, 134 may include a therapeutic agent that includes a DOAC, such as, but not limited to, apixaban, rivaroxaban, edoxaban, dabigatran, betrixaban, and argatroban. However, other beneficial therapeutic agents may include, but are not limited to, anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

More specific drugs or therapeutic agents include paclitaxel, rapamycin, sirolimus, everolimus, tacrolimus, heparin, diclofenac, aspirin, Epo D, dexamethasone, estradiol, halofuginone, cilostazol, geldanamycin, ABT-578 (Abbott Laboratories), trapidil, liprostin, actinomycin D, Resten-NG, Ap-17, abciximab, clopidogrel, Ridogrel, beta-blockers, bARKct inhibitors, phospholamban inhibitors, and SERCA 2 gene/protein, resiquimod, imiquimod (as well as other imidazoquinoline immune response modifiers), human apolipoproteins (e.g., AI, AII, AIII, AIV, AV, etc.), vascular endothelial growth factors (e.g., VEGF-2), as well as derivatives of the forgoing, among many others, and/or combinations thereof.

In some embodiments, the drug may be a macrolide immunosuppressive (limus) drug. In some embodiments, the macrolide immunosuppressive drug is rapamycin, biolimus (biolimus A9), 40-O-(2-Hydroxyethyl) rapamycin (everolimus), 40-O-Benzyl-rapamycin, 40-O-(4'-Hydroxymethyl) benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4 (S)-yl)-prop-2'-en-1'-yl]-rapamycin, (2':E,4'S)-40-O-(4',5'-Dihydroxypent-2'-en-1'-yl)-rapamycin, 40-O-(2-Hydroxy) ethoxycar-bonylmethyl-rapamycin, 40-O-(3-Hydroxy) propyl-rapamycin, 40-O-(6-Hydroxy) hexyl-rapamycin, 40-O-[2-(2-Hydroxy) ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino) acetoxy]ethyl-rapamycin, 40-O-(2-N-Imidazolylacetoxy) ethyl-rapamycin, 40-O-[2-(N-Methyl-N'-piperazinyl) acetoxy]ethyl-rapamycin, 39-O-Desmethyl-39,40-O,O-ethylene-rapamycin, (26R)-26-Dihydro-40-O-(2-hydroxy) ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl) rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), or derivative, isomer, racemate, diastereoisomer, prodrug, hydrate, ester, or analog thereof. Other drugs may include anti-inflammatory agents such as dexamethasone, prednisolone, corticosterone, budesonide, estrogen, sulfasalazine, mesalamine, and analogues thereof; antineoplastic/antiproliferative/anti-miotic agents such as paclitaxel, 5-fluorouracil, cisplatin, vinblastine, vincristine, epothilones, endostatin, angiostatin, thymidine kinase inhibitors, and analogues thereof; anesthetic agents such as lidocaine, bupivacaine, ropivacaine, and analogues thereof; anti-coagulants; and growth factors.

In some instances, a drug coated medical device 10, 110 with a drug coating 34, 134 that provides localized sustained delivery of a direct anti-coagulant may reduce the risk of venous occlusions (such as, but not limited to, thrombus) and may block stimulation of inflammatory cytokines which may reduce fibrosis and intimal thickening. For example, the drug coated medical devices 10, 110 described herein uses direct oral anticoagulants (DOACs) (which are typically taken orally and used systemically) and provides them only on the surface of the device where they are needed, thus providing the advantage of reducing the potential adverse effects of systemic OAC therapy. A drug coated medical device 10, 110 with a drug coating 34, 134 may be used to treat persistent venous occlusions by both preventing thrombus and intimal thickening. It is contemplated that the drug coated medical device 10, 110 may be delivered to a treatment location immediately after the removal of a DVT, to a site of persistent venous occlusion, etc.

In some cases, rivaroxaban may be the drug used. Rivaroxaban, which is also known as (S)-5-Chloro-N-((2-oxo-3-(4-(3-oxomorpholino)phenyl)oxazolidin-5-yl)methyl) thiophene-2-carboxamide, has the following chemical structure:

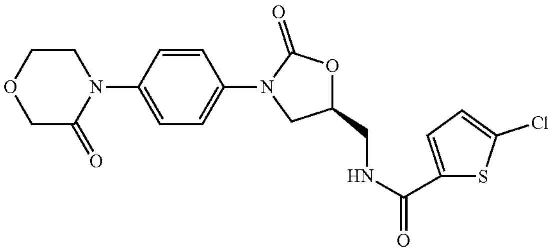 [SMILES: O=C(NC[C@H]1CN(c2ccc(N3CCOCC3=O)cc2)C(=O)O1)c1ccc(Cl)s1]

In some instances, the drug coating 34, 134 may include individual drug particles that are encapsulated with one or more excipients. The drug particles may include crystals of the drug, for example. Drug crystals may be formed in a variety of ways, for example. In some cases, a drug or other therapeutic agent may be available in an amorphous form, and a variety of processes may be used to convert an amorphous drug or other therapeutic agent into a crystalline drug or other therapeutic agent. In other examples, the therapeutic agent may be available in crystalline form. In yet other examples, the therapeutic agent may become crystalline during the process of making and applying the drug coating 34, 134. However, in some cases, the individual drug particles need not be encapsulated.

A medical device 10, 110, or portions thereof, may be coated with a therapeutic composition 34, 134. As an example, the therapeutic composition may include one or more therapeutic agents, such as, but not limited to, rivaroxaban. Rivaroxaban crystals may be mixed with, dispersed in, and/or coated with an excipient or a mixture of excipients. Excipients can be used to enhance the durability of the drug coating 34, 134, facilitate drug transfer to the treatment location, and/or control drug dissolution. In some embodiments, one or more additional therapeutic agents may be provided in addition to rivaroxaban. For example, paclitaxel may be added to the therapeutic composition. In other examples, paclitaxel may be provided in a separate layer as an additional separate therapeutic composition. In some instances, the medical device 10, 110, or portions thereof, may be contacted with the coating composition in order to form a coating on the medical device. In some instances, the medical device 10, 110, or a portion thereof, may be dipped into the coating composition. In some cases, vapor deposition may be used to transfer the coating composition to the medical device 10, 110. In some cases, a roller coating process may be used to transfer the coating composition to the medical device 10, 110. These are just examples. In some cases, the coating composition may be sprayed onto the medical device 10, 110, or may be sprayed onto a particular portion or region of the medical device 10, 110.

When the medical device 10 includes an inflatable balloon 14, for example, the coating composition may be sprayed onto at least a portion of the outer surface of the inflatable balloon 14 in order to be able to subsequently transfer at least a portion of the drug coating 34 to blood vessel walls. Alternative coating processes may be used such as dip coating, roller coating, syringe coating, vapor deposition, and/or the like, and/or other suitable coating processes. There may be little or no benefit to applying the coating composition to other portions of the medical device such as a balloon catheter shaft because the balloon catheter shaft may make incidental contact at best with the blood vessel walls, for example.

When the medical device is or includes an expandable stent 110, the coating composition may be sprayed onto at least a portion of the outer surface 144 of the expandable stent 110 in order to be able to subsequently transfer at least a portion of the drug directly to blood vessel walls. When the coating compositions 134 is deposited on an outer surface of the expandable stent 110, the coating composition 134 may be held in apposition with the tissue to be treated. There may be a benefit to eluting at least a portion of the drug into the blood flowing through the expandable stent, as this can provide a local therapeutic dose of the drug across the vessel walls between stent struts and downstream of where the expandable stent 110 is deployed. Thus, the coating composition may be applied to the interior surface 146 and/or the lateral sidewalls of the expandable stent 110.

In addition to the therapeutic agent, the coating composition 34, 134 may further include one or more excipients. Excipients can be used to enhance the durability of the drug coating 34, 134, facilitate drug transfer to the lesion, and/or control drug dissolution. It is contemplated that inflatable balloons 14 and stents 110 may require different excipients due to the difference in use. For example, an inflatable balloon 14 may require an excipient that facilitates transfer of the coating composition 34 from the balloon 14 to the vessel wall while the coating composition 134 of the stent 110 may remain thereon. An example excipient may include poly(vinylidene fluoride)-co-hexafluoropropylene (PVDF-HFP) which can be formed as a porous membrane. PVDF-HFP has the following chemical structure:

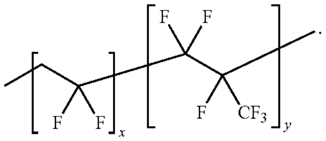

Another example excipient may include acetyl tri-butyl citrate (ATBC), which in some cases may be referred to by its IUPAC name of tributyl 2-acetyloxypropane-1,2,3-tricarboxylate. ATBC has the following chemical structure:

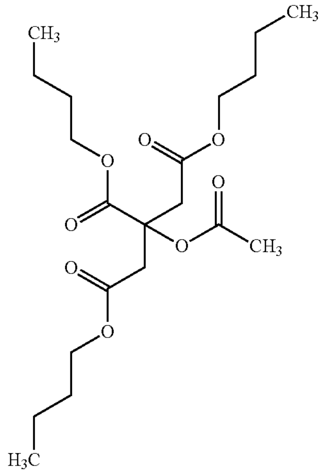 [SMILES: CCCCOC(=O)CC(CC(=O)OCCCC)(OC(C)=O)C(=O)OCCCC]

Another example excipient may include polylactic acid (PLA). PLA has the following chemical structure:

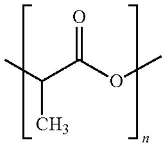

Other example excipients may include, but are not limited to, acetyl tri-butyl citrate (ATHC), poly-DL-lactide (PDLLA), poly-L-lactide (PLLA), poly-D-lactide (PDLA), poly(lactic-co-glycolic acid) (PLGA), etc. It is contemplated that the release rate of rivaroxaban can be increased or decreased based on the degradation rate of the excipient. For example, PLGA may degrade faster than PLA. By using a faster degrading polylactide/glycolide copolymer (PLGA) the release rate of rivaroxaban can be increased. The release from PLGA can be controlled by controlling the lactide to glycolide ratio and polymer molecular weight.

ATBC may be a plasticizer or plasticizing agent which helps hold the drug particles onto the balloon 14 prior to deployment and facilitates transfer to the vessel during balloon deployment and may slow the dissolution of the therapeutic agent. In some examples, additional components may also be used in the coating composition 34, 134. In some cases, an antioxidant, such as, but not limited to, butylated hydroxytoluene (BHT) may be used in the composition.

A challenge with formulating a rivaroxaban-based drug coated balloon is the relatively high water solubility of rivaroxaban compared to paclitaxel and olimus based drug coated balloons. Both crystalline paclitaxel and everolimus are soluble in water to about the range of 0.2-0.5 micrograms (μg) drug per milliliter (mL) water. Crystalline rivaroxaban is soluble in water to about 3 μg drug per mL water. As can be seen crystalline rivaroxaban is approximately 10 times more water soluble than paclitaxel and everolimus. This may pose a challenge to formulating a rivaroxaban based drug coated balloon 14 with sustained tissue release using excipients used in many prior drug coated balloons. For example, rivaroxaban drug coated balloons using ATBC or ethyl cellulose as excipients show rapid drug dissolution in an in-vitro drug release test.

In an illustrative example, the drug coating 34 may include PLA as the excipient. The therapeutic agent, such as, but not limited to, an anticoagulant such as a direct oral anticoagulant (DOAC) such as rivaroxaban, may be contained within microspheres of PLA, or another biodegradable polymer. The microsphere may range in size from about 1 μm to about 20 μm in diameter. The microspheres may container in the range of about 5 weight percent to about 45 weight percent therapeutic agent and in the range of about 55 weight percent to about 95 weight percent PLA. In some examples, ATBC may be provided as an additional excipient in the drug coating to help anchor the microspheres to the vessel walls during deployment of the inflatable balloon 14. In other examples, polydopamine may be provided as an additional excipient in the drug coating 34 to help anchor the microspheres to the vessel walls during deployment of the inflatable balloon 14. For example, the microspheres may be coated with polydopamine. An illustrative polydopamine coating is described in commonly assigned U.S. Patent Publication Number 2016/0331564, titled DRUG COATED MEDICAL DEVICES, the disclosure of which is hereby incorporated by reference.

In another example, the drug coating 134 may include a hemocompatible polymer such as, but not limited to, poly (vinylidene fluoride)-co-hexafluoropropylene (PVDF-HFP) and a therapeutic agent such as an anticoagulant such as a direct oral anticoagulant (DOAC). In some examples, the PVDF-HFP may have a VDF to HFP ratio of 85/15. However, this is not required. Other ratios may be used as desired. The therapeutic agent may form crystalline particles within a continuous PVDF-HFP matrix. The resulting drug coating 134 may be applied to a surface of the stent 110 to act as a drug depot for sustained localized release.

It is contemplated that the surface area of the stent 110 and/or a time period over which the device 110 is in situ may determine, at least in part, how long the drug coating 134 releases the drug. For example, a stent 110 which is implanted into the body may release the drug for a longer period of time than a balloon which is temporality inflated and transfers the drug coating 34 to the vessel wall. In some cases, the surface area of the device 14, 110 may be adjusted to provide the desired duration of drug release. For example, the number of struts in the strut framework 136 may be increased to increase the surface area of the stent 110 and thus increase the volume of drug coating (and thus drug) that can be placed on the stent 110. Alternatively, or additionally, the surface area of the stent 110 may be increased by providing a stent covering on an outer and/or inner surface thereof. If so provided, the stent covering may cover an entirety of the stent 110 or one or more portions thereof. In some examples, a stent 110 may be sized and shaped to provide the ability to build in drug reservoirs to provide long duration (e.g., about 1 year) release of DOAC and other drugs to locally treat PTS and other vessel disease.

In one embodiment, a polymer coating such as PVDF-HFP, and one or more DOACs are dissolved in a solvent suitable for dissolving the polymer and drug. In some examples, the solvent may be a blend of acetone and N,N-dimethyl formamide (DMF). However, other solvents such as, but not limited to, N,N-dimethyl acetamide (DMAc), dimethylsulfoxide (DMSO) and N-methyl pyrrolidone (NMP), may be used. This solution may be applied directly to the stent 110 by a dip coating or spray process. Spray coating may result in the drug coating 134 being disposed only on one surface of the stent 110, although this is not required. It is contemplated that an entirety of the stent 110 may be coated with the drug coating 134. In other examples, less than an entirety of the stent 110 may be coated with the drug coating 134. The drug coating 134 may be applied to achieve a coating density of between 100-4,000 nanograms (ng) drug per square millimeter (mm) (ng/$mm^2$) on the surface of the stent 110 (based on vessel surface area). The drug coating may include in the range of about 5 weight percent to about 45 weight percent therapeutic agent and in the range of about 55 weight percent to about 95 weight percent PVDF-HFP. It is contemplated that a significantly thicker coating may be achievable when the drug coating 134 is disposed on a stent 110 compared to coating a balloon 14. The thickness of the drug coating 34 on the balloon 14 may be limited due to the impact of folding and unfolding of the balloon 14 during loading and deployment of the balloon 14. A thicker drug coating 34 on a balloon 14 may crack and flake or impede the folding and unfolding process. Drug coatings 134 on a stent 110 may have a thickness of up to 10 μm and anticoagulant content of in the range of about 100-300 micrograms (μg) may be achievable on a stent 110. The significantly thicker coatings on a stent 110, as well as the increased contact time, may lead to a longer drug release time compared to a balloon 14 or a thinner drug coating 34, 134. In another example, the amount of drug contained in the coated or stent 110 device may about 100-4000 ng/$mm^2$. It is contemplated that a drug coating 134 including PVDF-HFP and a DOAC, such as rivaroxaban, may release in the range of about 40-80% of the therapeutic agent in about 7-60 days when the device 110 is implanted.

In a further example, a DOAC, such as rivaroxaban, may be dissolved in a solvent and a polymer excipient. The subsequent mixture may then then be deposited on a stent 110 by spray or dip coating. A top layer of a polymer that contains no drug may deposited over the drug coating 110 to further modulate the drug release rate. In some examples, the polymer topcoat may include PVDF-HFP. It is contemplated that increasing the weight percent of the polymer topcoat relative to the weight of the drug coating 134 may slow a release of the therapeutic agent.

It is contemplated that when the drug coating 34 is applied to a balloon 14, the DOAC crystals, such as rivaroxaban crystals, may embed in the tissue to be treated. Alternatively, or additionally, the excipient may be chosen to help the drug coating 34 adhere to the treatment location. In yet another example, the DOAC, such as rivaroxaban, may be incorporated into a biodegradable polymer microsphere, where the microsphere is embedded in the tissue to be treated and the biodegradable polymer controls the release of the drug into the tissue. Additionally, an additional excipient, such as, but not limited to ATBC, may be chosen to help the microsphere to adhere to the treatment location.

It is contemplated that any of the drug coating compositions described herein may disposed over a primer layer. The primer layer may be applied directly to the balloon 14 and/or stent 110 prior to applying the drug coating composition 34, 134. The primer layer may be applied to the balloon 14 and/or stent 110 using coating processes, such as, spray coating, dip coating, roller coating, vapor deposition, and/or the like, and/or other suitable coating processes. In some examples, the primer layer may be a polymer dissolved in a solvent or mixture of solvents. An illustrative primer layer for a stent 110 may include poly(butyl methacrylate) (PBMA) (2% solids) dissolved in a solvent mixture that includes in the range of about 70% acetone and 30% cyclohexanone.

Process for Forming Crystalline Rivaroxaban

Crystalline rivaroxaban may be generated by crystallization of the rivaroxaban from a solution of a mixture of N,N-dimethyl formamide (DMF) and water. Crystalline rivaroxaban may also be generated by slowly adding a solution of rivaroxaban in DMF (1 to 4 wt % solids) into a large excess of deionized (DI) water.

Experimental Results

Figure 8:
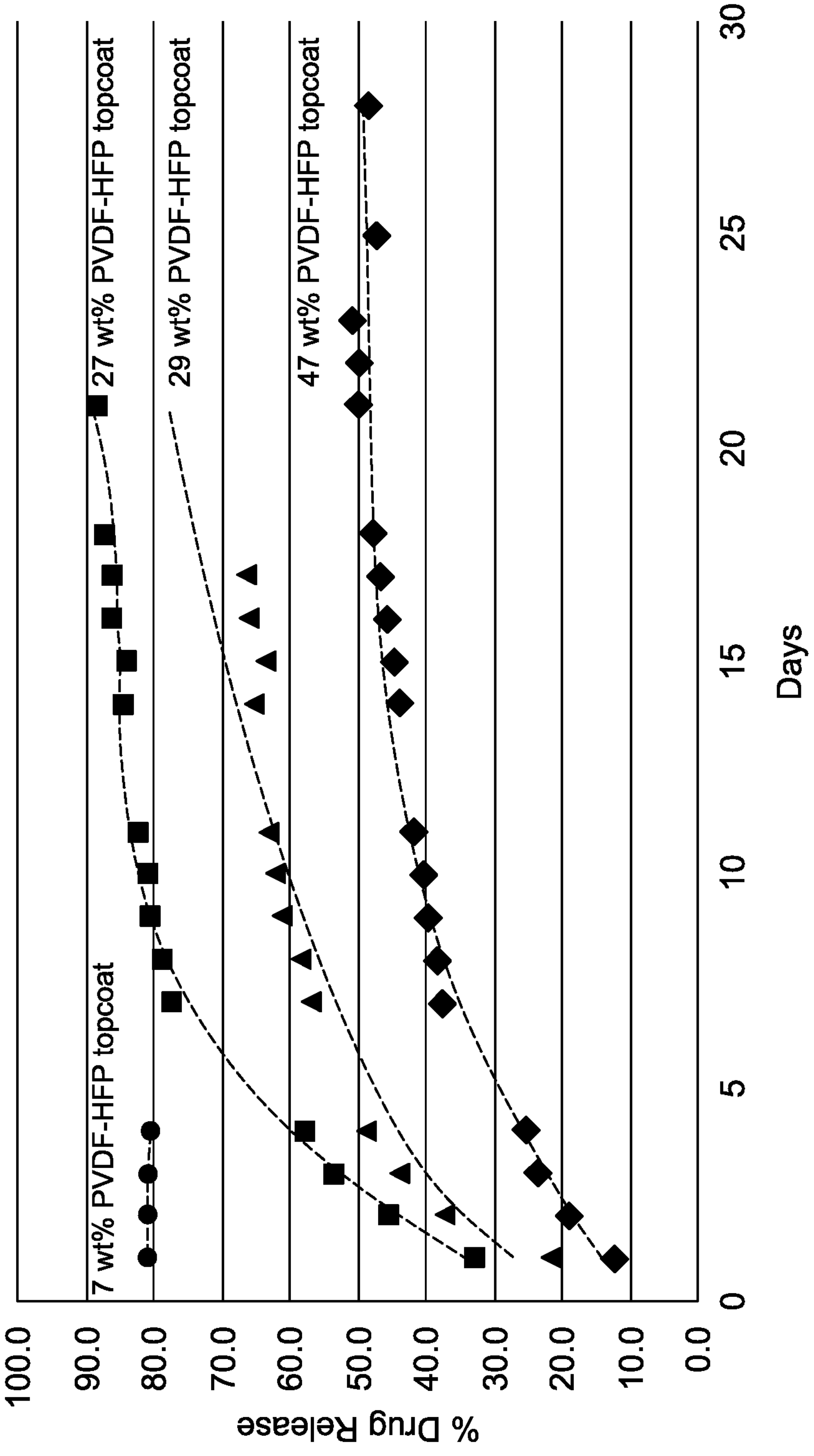
FIG. 8 is a graphical representation of experimental data.

FIG. 8 is a graphical representation of experimental data providing relative drug release rates when stents were coated with a base coat of a drug coating including 60 weight percent PVDF-HFP and 40 weight percent rivaroxaban. Each drug coating was coated with a topcoat of PVDF-HFP having varying weight percents relative to the drug coating.

Innova™ self-expanding stents (8 mm×20 mm; commercially available from Boston Scientific®) were spray coated with several PVDF-HFP/rivaroxaban coating formulations. The coatings consisted of a base coat made up of 60/40 (wt/wt) PVDF-HFP/rivaroxaban. The base coat was sprayed from a 2% (wt/wt) solution of the polymer/drug in 60/40 acetone/DMF. The base coat was spray overcoated with PVDF-HFP at different thicknesses. As the stents were all of the same size, increasing the thickness of the PVDF-HFP topcoat also increased the weight of the topcoat. The overcoat was sprayed from a solution of 2 wt % solids of PVDF-HFP in acetone. Table 1 below shows the formulations coated. In-vitro drug release from the coated stents was performed by incubating the stents in phosphate buffered saline (PBS) (pH~7)/TWEEN® 20 solution at 37° C. and 120 rpm on an orbital shaker incubator. Drug elution was quantified by analyzing the phosphate buffered saline solution using high-performance liquid chromatography (HPLC) at various timepoints. The drug release curves are shown in FIG. 8.

TABLE 1

Coating formulations of drug coated stents.

| Sample | Base Coat Weight (mg) | Base Coat Composition | Topcoat Weight (mg) | Topcoat Composition | Weight % Topcoat (topcoat to basecoat) |
|---|---|---|---|---|---|
| 1 | 4.2 | 60 wt % PVDF-HFP; 40 wt % rivaroxaban | 0.31 | 100% PVDF-HFP | 7.2 |
| 2 | 4.1 | 60 wt % PVDF-HFP; 40 wt % rivaroxaban | 1.1 | 100% PVDF-HFP | 27 |
| 3 | 4.1 | 60 wt % PVDF-HFP; 40 wt % rivaroxaban | 1.2 | 100% PVDF-HFP | 29 |
| 4 | 4.2 | 60 wt % PVDF-HFP; 40 wt % rivaroxaban | 2.0 | 100% PVDF-HFP | 47 |

FIG. 8 illustrates how drug release can be controlled by varying the weight and thickness of PVDF-HFP topcoat. A range of drug release durations from approximately 1 day to more than 30 days are possible by tailoring the topcoat thickness and/or weight. For example, as can be seen in FIG. 8, increasing the weight percent of the topcoat, and thus the thickness, slowed the release of the rivaroxaban. For example, the sample having a topcoat of 7 weight percent PVDF-HFP released approximately 80% of the rivaroxaban within a day. The sample having a topcoat of 27 weight percent PVDF-HFP released approximately 80% of the rivaroxaban within about 9 days and 90% of the rivaroxaban within about 21 days. The sample having a topcoat of 29 weight percent PVDF-HFP released approximately 80% of the rivaroxaban within about 21 days. The sample having a topcoat of 29 weight percent PVDF-HFP released approximately 80% of the rivaroxaban within about 21 days. The sample having a topcoat of 47 weight percent PVDF-HFP released approximately 50% of the rivaroxaban within about 28 days.

Figure 9:
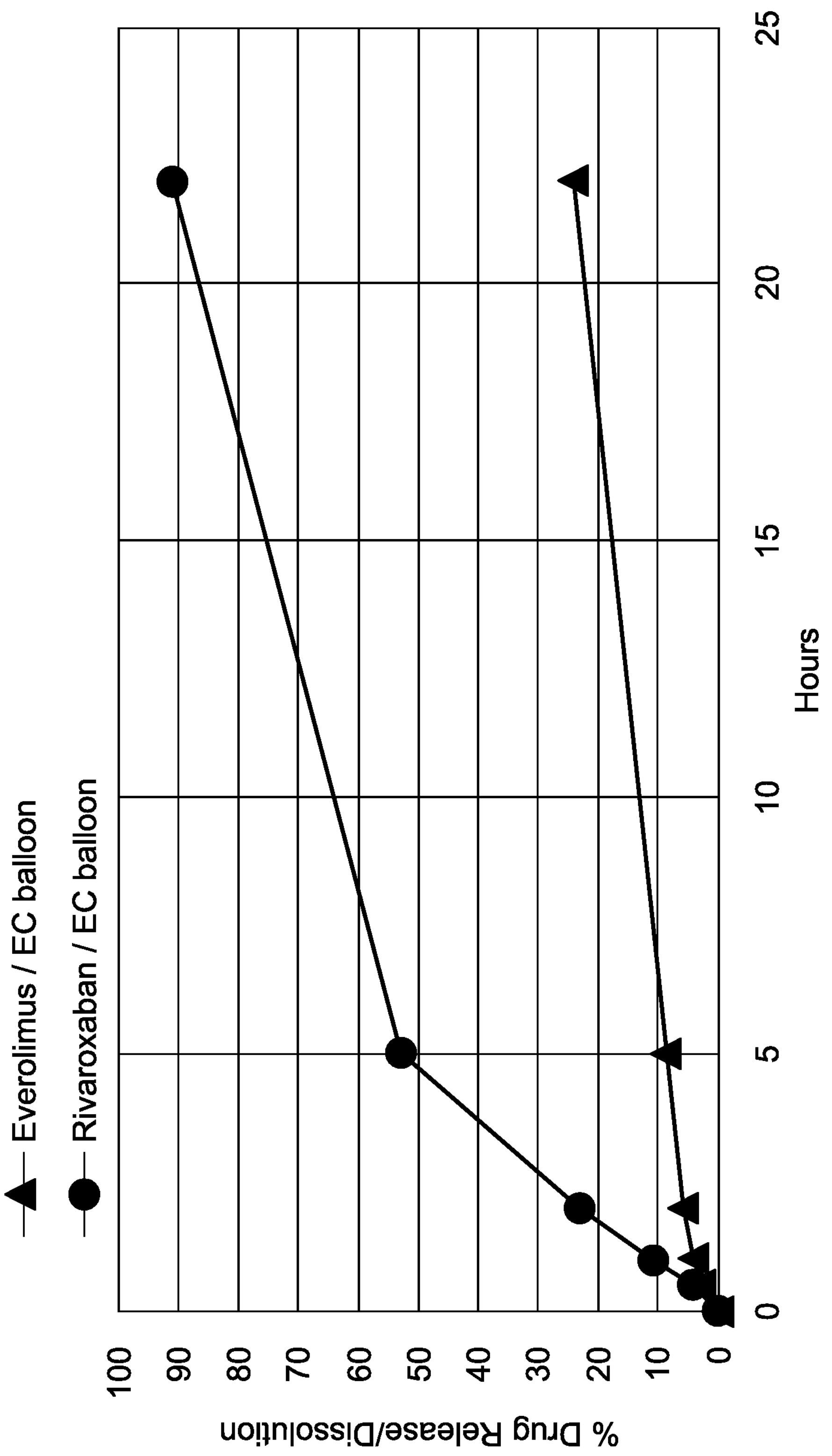
FIG. 9 is a graphical representation of experimental data.

FIG. 9 shows drug release from a rivaroxaban coated balloon compared to an everolimus based balloon when using ethyl cellulose as an excipient. Within 22 hours, greater than 90% of the rivaroxaban had been released/dissolved, whereas with the everolimus based balloon only about 24% of the drug is released/dissolved. In order to achieve a longer release/dissolution profile the drug was incorporated into the slowly degradable bioabsorbable polymer matrix polylactide (PLA) in the form of microspheres. The resulting microspheres can then be coated onto a balloon with an excipient such as ATBC or ethyl cellulose, where the excipient acts to adhere the beads to the surface of the balloon and also aids in transferring the beads to the vessel during deployment.

Figure 10:
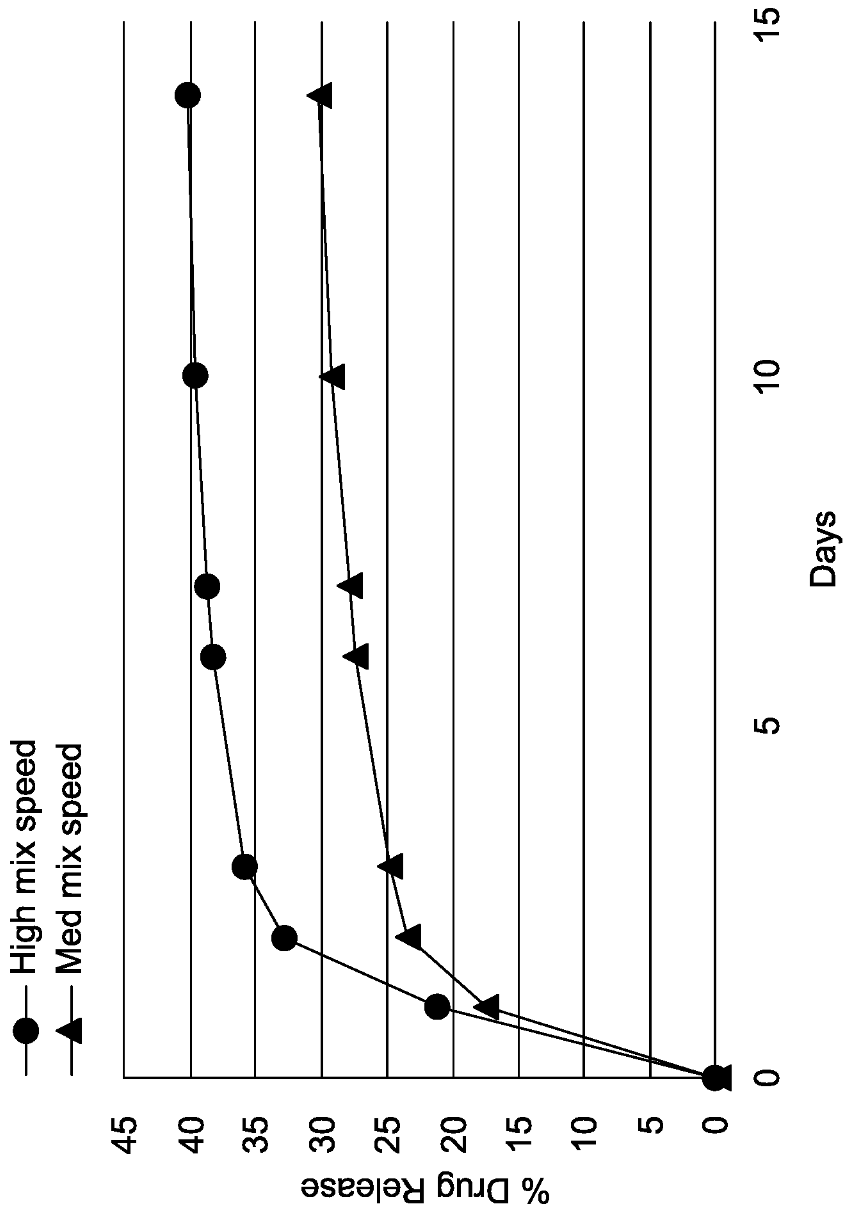
FIG. 10 is a graphical representation of experimental data.

PLA/rivaroxaban microspheres were prepared by first dissolving PLA 10 (available from Evonik based in Essen, Germany) and rivaroxaban at a ratio of 91/9 (wt/wt) in a 75/25 (wt/wt) mixture of dichloromethane and dimethylformamide. 0.5 mL of the PLA/rivaroxaban solution was added to 10 mL of 2% aqueous poly (vinyl alcohol) (PVA) (146,000 to 186,000 molecular weight (MW), 87 to 89% Hydrolyzed) while mixing using a homogenizer. Beads were prepared at three different mixer revolutions per minute (rpm) to get a range of microsphere sizes. For example, a slower mixer speed may result in a larger microsphere (bead) size. After mixing for 2 minutes, the bead solution was added to 150 mL of 0.1% PVA in water and allowed to stir with a magnetic stir bar for 2 hours. The resulting beads were collected by filtration and dried under vacuum at room temperature for 3 days. The drug content (rivaroxaban) of the beads was determined by HPLC. The drug release was determined by incubating the beads in phosphate buffered saline (PBS) (PH~7)/TWEEN® 20 solution at 37° C. and 120 rpm on an orbital shaker incubator. Drug content of the PBS was measured by HPLC. Table 2 shows the drug content and bead size data. FIG. 10 shows the drug release data for the PLA based beads created at medium mix speed and high mix speed. Within 6 days approximately 38% of the drug was released from the smaller microspheres (e.g., formed at high mixing speeds) and approximately 27% of the drug was released from the medium microspheres (e.g., formed at medium mixing speeds). Thus, smaller microspheres may initially release the drug at a higher rate. The release rate slowed after about 6 days but the microspheres continued releasing the drug. For the PLA based microspheres, it is estimated that the microspheres will release rivaroxaban for greater than 45 days. The release rate of rivaroxaban can be increased by using a faster degrading polylactide/glycolide copolymer (PLGA). The release from PLGA can be controlled by controlling the lactide to glycolide ratio and polymer molecular weight.

TABLE 2

PLA/Rivaroxaban microsphere data

| Bead sample | % Drug recovery | Bead size (μm) |
|---|---|---|
| Low mix speed | 81 | 10-40 |
| Med mix speed | 79 | 10-20 |
| High mix speed | 85 | 5-15 |

The materials that can be used for the various components of the medical devices described herein may include those commonly associated with medical devices. The medical devices described herein may include components that may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical devices described herein may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical devices described herein in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical devices described herein to achieve the same result.

In some embodiments, a degree of Magnetic Resonance Imaging (MRI) compatibility is imparted into the medical devices described herein. For example, the medical devices described herein, or portions thereof, may be made of a material that does not substantially distort the image and create substantial artifacts (i.e., gaps in the image). Certain ferromagnetic materials, for example, may not be suitable because they may create artifacts in an MRI image. The medical devices described herein, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. A method for manufacturing a drug coating composition, the method comprising:

dissolving polylactic acid (PLA) or poly(lactic-co-glycolic acid) (PLGA) and rivaroxaban in a mixture of dichloromethane and dimethylformamide to form a first solution;

adding the first solution to aqueous poly (vinyl acid) PVA while mixing to form a bead solution;

filtering the bead solution to collect a plurality of microspheres; and drying the plurality of microspheres.

2. The method of claim 1, wherein the PLA or PLGA and rivaroxaban are dissolved at a ratio of in the range of about 85 to 95 weight percent PLA or PLGA to about 5 to about 15 weight percent rivaroxaban.

3. The method of claim 1, wherein the mixture of dichloromethane and dimethylformamide is about 75 weight percent dichloromethane and about 25 weight percent dimethylformamide.

4. The method of claim 1, wherein the aqueous PVA is about 2% PVA.

5. The method of claim 1, further comprising adding the bead solution to a 0.1% solution of aqueous PVA and mixing for a first period of time.

6. The method of claim 1, wherein drying the plurality of microspheres includes drying the microspheres under vacuum at room temperature for a second period of time.

* * * * *